(12) United States Patent
Lim et al.

(10) Patent No.: US 8,722,027 B2
(45) Date of Patent: May 13, 2014

(54) METHOD FOR PREPARING BROUSSONETIA KAZINOKI EXTRACT

(75) Inventors: Hyung Jun Lim, Seoul (KR); Jin Young Lee, Yongin-si (KR); Sun Young Park, Yongin-si (KR); Soon Ae An, Yongin-si (KR); Chan Woo Lee, Yongin-si (KR); Eun Joo Kim, Yongin-si (KR); Jun Oh Kim, Yongin-si (KR); Sang Hun Han, Suwon-si (KR); Han Kon Kim, Suwon-si (KR)

(73) Assignee: Amorepacific Corporation (KR)

( * ) Notice: Subject to any disclaimer, the term of this patent is extended or adjusted under 35 U.S.C. 154(b) by 0 days.

(21) Appl. No.: 13/704,369

(22) PCT Filed: Jun. 15, 2011

(86) PCT No.: PCT/KR2011/004380
§ 371 (c)(1),
(2), (4) Date: Dec. 14, 2012

(87) PCT Pub. No.: WO2011/159098
PCT Pub. Date: Dec. 22, 2011

(65) Prior Publication Data
US 2013/0084258 A1 Apr. 4, 2013

(30) Foreign Application Priority Data

Jun. 18, 2010 (KR) .................. 10-2010-0057943
Jun. 14, 2011 (KR) .................. 10-2011-0057478

(51) Int. Cl.
*A61K 8/00* (2006.01)
*C07C 39/12* (2006.01)

(52) U.S. Cl.
USPC ............................................ 424/62; 568/729

(58) Field of Classification Search
USPC ........................................................ 424/62
See application file for complete search history.

(56) References Cited

U.S. PATENT DOCUMENTS

| | | | | |
|---|---|---|---|---|
| 5,804,613 | A * | 9/1998 | Beall et al. .................. | 523/200 |
| 2004/0166069 | A1* | 8/2004 | Gupta ............................ | 424/59 |
| 2008/0132581 | A1* | 6/2008 | Jia et al. ....................... | 514/729 |

FOREIGN PATENT DOCUMENTS

| | | |
|---|---|---|
| KR | 1020060121496 A | 11/2006 |
| KR | 100858917 B1 | 9/2008 |
| WO | 2010062087 A2 | 6/2010 |

OTHER PUBLICATIONS

Jang, "Melanogenesis Inhibitor from Paper Mulberry", Cosmetics & Toiletries magazine, vol. 112, 59-62, 1997.*
Wang, "Recent advances in extraction of nutraceuticals from plants", Trends in Food Science & Technology, vol. 17, 300-312, 2006.*
WISC, "Recrystallization", University of Wisconsin, p. 1-4, 2004, http://www.chem.wisc.edu/courses/342/Fa112004/Recrystallization.pdf.*
Amelio "Paper Mulberry and its preparations as Tyrosinase Inhibitors and Skin Lightening Agents", Bio-Botanica. Inc, 2001.*
Lu, "Effective two-dimensional counter-current chromatographic method for simultaneous isolation and purification of oridonin and ponicidin from the crude extract of Rabdosia rubescens", Journal of Chromatography A, 1146, pp. 125-130, 2007).*
Baek, "Tyrosinase inhibitory effects of 1,3-diphenylpropanes from Broussonetia kazinoki", Bioorganic & Medicinal Chemistry 17, pp. 35-41, 2006.*
Written Opinion for International Application No. PCT/KR2011/004380 dated Feb. 10, 2012.
International Search Report with English Translation for International Application No. PCT/KR2011/004380 dated Feb. 10, 2012.
Chinese Office Action for Application No. 201180031528.X dated Nov. 12, 2013.
Baek, Y, et al, "Tyrosinase inhibitory effects of 1,3-diphenylpropanes from Broussonetia kazinoki"., Bioorganic & Medicinal Chemistry, 2009, vol. 17, pp. 35-41.

* cited by examiner

*Primary Examiner* — David J Blanchard
*Assistant Examiner* — John P Nguyen
(74) *Attorney, Agent, or Firm* — Cantor Colburn LLP

(57) ABSTRACT

The present invention provides a method for preparing a *Broussonetia kazinoki* extract, comprising the following steps: solvent extracting *Broussonetia kazinoki*; isolating the *Broussonetia kazinoki* extract, extracted in the previous step; and crystallizing the *Broussonetia kazinoki* extract isolated in the previous step. It is possible to prepare a *Broussonetia kazinoki* extract having a remarkable skin whitening effect and excellent stability through the method for preparing a *Broussonetia kazinoki* extract.

8 Claims, 2 Drawing Sheets

METHOD FOR PREPARING BROUSSONETIA KAZINOKI EXTRACT

TECHNICAL FIELD

The present invention relates to a method for preparing a *Broussonetia kazinoki* extract.

BACKGROUND ART

Melanin that is a dark brown pigment functions to block UV rays, and thus functions to protect the skin from UV rays. Thus, when the skin is exposed to UV rays, a large amount of melanin is produced in the body in order to protect the skin. The skin color is determined by the amount of melamine. The more the amount of melanin, the darker the skin color. Thus, the production of a large amount of melanin causes discoloration, spots, freckles, dark spots and so on. Accordingly, substances that inhibit melanin production can have skin whitening effects.

Tyrosinase is an enzyme that converts tyrosine to dopa which is then oxidized to dopa quinine. Dopa quinine is then polymerized to form melanin. In other words, tyrosinase acts as an enzyme that catalyzes melanin production, and thus substances that inhibit tyrosinase can have skin whitening effects.

DISCLOSURE

Technical Problem

An object of the present invention is to provide a method for preparing a *Broussonetia kazinoki* extract which contains an active ingredient at high purity while showing excellent stability. Another object of the present invention is to provide a *Broussonetia kazinoki* extract which is prepared by the above method, contains a high purity of a skin whitening active ingredient and has excellent inhibitory effects on melanin production and tyrosinase activity. Still another object of the present invention is to provide a skin external composition which contains the *Broussonetia kazinoki* extract and has excellent skin whitening effects.

Technical Solution

In one aspect, the present invention provides a method for preparing a *Broussonetia kazinoki* extract, the method comprising the steps of: (1) extracting *Broussonetia kazinoki* with a solvent; (2) allowing the *Broussonetia kazinoki* extract resulting from step (1) to stand; and (3) crystallizing the *Broussonetia kazinoki* extract resulting from step (2).

In another aspect, the present invention provides a *Broussonetia kazinoki* for skin whitening prepared by the above method.

In still another aspect, the present invention provides a skin external composition containing the *Broussonetia kazinoki* extract.

Advantageous Effects

A method for preparing a *Broussonetia kazinoki* extract according to one aspect of the present invention can prepare a *Broussonetia kazinoki* extract which contains an active ingredient at high purity while showing excellent stability.

A *Broussonetia kazinoki* extract according to another aspect of the present invention is prepared by the above method and has excellent skin whitening effects while showing excellent stability.

A skin external composition according to still another aspect of the present invention contains the *Broussonetia kazinoki* extract and has excellent skin whitening effects.

MODE FOR INVENTION

Figure 1:
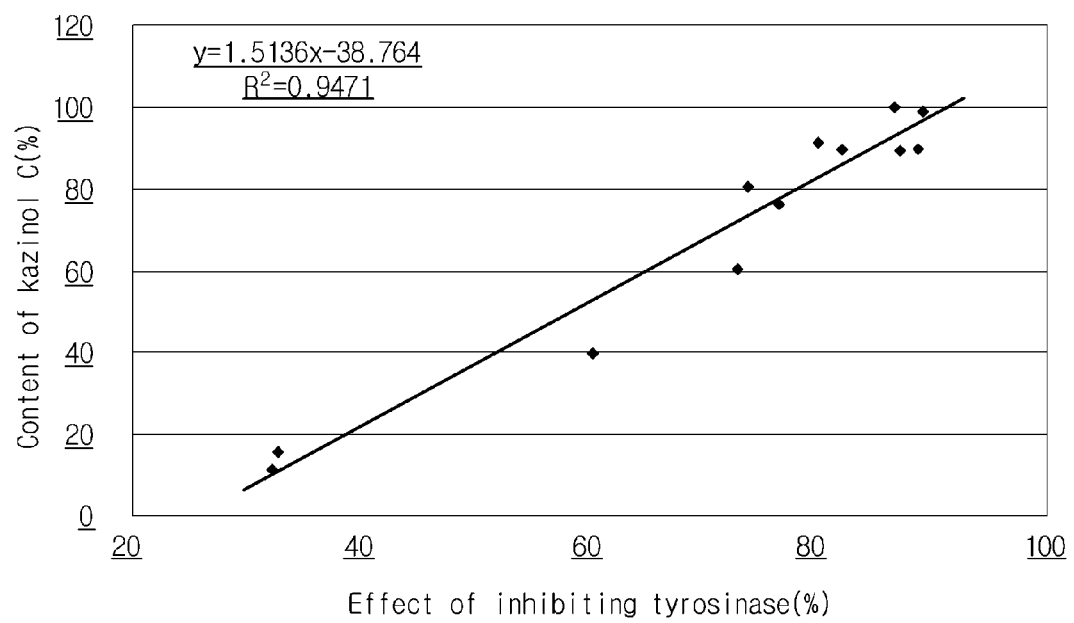
FIG. 1 is a graph showing the relationship between the kazinol C content (%) and tyrosinase inhibitory effect (%) of a *Broussonetia kazinoki* extract.

As used herein, the term "extract" is meant to include all materials obtained by extracting components from natural materials by any method. Examples of the extract include solvent-soluble components extracted from natural materials using water or organic solvents, and materials obtained by extracting specific components (e.g., oil) from natural materials.

As used herein, the term "skin" is meant to include not only a tissue covering the surface of the face or body of an animal, but also scalp and hair.

Hereinafter, the present invention will be described in detail.

It is known that a *Broussonetia kazinoki* extract contains kazinol F as a skin whitening active ingredient, which shows a skin whitening effect by inhibiting tyrosinase activity. Kazinol C contained in the *Broussonetia kazinoki* extract is known to have an excellent tyrosinase inhibitory effect compared to kojic acid. However, the skin whitening active ingredients have unstable activities which make it difficult to commercialize the extract. Accordingly, if there is a method for preparing a *Broussonetia kazinoki* extract which contains skin whitening active ingredients at high purifies while showing stabilities, a *Broussonetia kazinoki* extract having an improved effect on the inhibition of tyrosinase activity can be prepared and will be easy to commercialize.

In one aspect, the present invention provides a method for preparing a *Broussonetia kazinoki* extract, the method comprising the steps of (1) extracting *Broussonetia kazinoki* with a solvent; (2) allowing the *Broussonetia kazinoki* extract resulting from step (1) to stand; and (3) crystallizing the *Broussonetia kazinoki* extract resulting from step (2).

*Broussonetia kazinoki* that is used in the method of the present invention is a plant belonging to the family Moraceae of the order Urticales. In one embodiment of the present invention, *Broussonetia kazinoki* includes *Broussonetia kazinoki Siebold*, *Wikstroemia trichotoma* or *Edgeworthia papyrifera*. In another embodiment of the present invention, *Broussonetia kazinoki* may be 1-3-year-old *Broussonetia kazinoki*. In still another embodiment of the present invention, *Broussonetia kazinoki* include one or more of all the portions of *Broussonetia kazinoki*. For example, *Broussonetia kazinoki* that is used in the present invention may include one or more of the leaf, flower, stem, branch, root, fruit and seed of *Broussonetia kazinoki*. In yet another embodiment of the present invention, *Broussonetia kazinoki* may be the root bark of *Broussonetia kazinoki*.

The method for preparing the *Broussonetia kazinoki* extract according to one embodiment of the present invention may further comprise, before the step of extracting *Broussonetia kazinoki* with the solvent, a step of preparing *Broussonetia kazinoki* by washing, drying and cutting. Specifically, the step of preparing *Broussonetia kazinoki* may comprise the processes of collecting *Broussonetia kazinoki*, cutting the root portion from the collected *Broussonetia kazinoki* and taking the root bark; washing the taken root bark with water; drying the washed root bark in a good ventilated place for 5-7 days; and cutting the dried root bark to a length of about 10-20 cm.

The method for preparing the *Broussonetia kazinoki* extract according to one embodiment of the present invention comprises a step of extracting *Broussonetia kazinoki* with a solvent. In one embodiment of the present invention, the solvent includes an organic solvent, particularly, alcohol, ether, ethyl acetate, acetone or chloroform, but is not limited thereto. The alcohol includes a $C_1$-$C_5$ lower alcohol, which includes any one or a mixture of two or more selected from the group consisting of methanol, ethanol, isopropyl alcohol, n-propyl alcohol, n-butanol and isobutanol, but is not limited thereto. In one embodiment of the present invention, the solvent may be used in an amount corresponding to 5-20 times the weight of *Broussonetia kazinoki*.

In one embodiment of the present invention, the extraction may be performed at a temperature between 50 and 100° C. for 1-10 hours. In another embodiment of the present invention, the extraction may be performed at a temperature between 60 and 90° C. for 3-8 hours. In yet another embodiment of the present invention, the extraction may be performed at a temperature between 60 and 80° C. for 4-6 hours.

The method for preparing the *Broussonetia kazinoki* extract according to one embodiment of the present invention may further comprise, after the step of extracting *Broussonetia kazinoki* with the solvent, a step of filtering the *Broussonetia kazinoki* extract to remove insoluble components. In one embodiment of the present invention, the filtration may be performed using filter paper.

The method for preparing the *Broussonetia kazinoki* extract according to one embodiment of the present invention may further comprise, after the step of filtering the *Broussonetia kazinoki* extract, a step of concentrating the filtered *Broussonetia kazinoki* extract. In one embodiment of the present invention, the concentration may be performed at a temperature of 80° C. or lower, particularly 60° C. or lower, until the volume of the extract reaches ¹⁄₁₀ to ¹⁄₂₀ of the volume before the concentration.

The method for preparing the *Broussonetia kazinoki* extract according to one aspect of the present invention comprises a step of allowing the *Broussonetia kazinoki* extract to stand. In one embodiment of the present invention, allowing the *Broussonetia kazinoki* extract to stand may be performed at a temperature between −5 and 25° C. for 1-40 hours. In another embodiment of the present invention, allowing the *Broussonetia kazinoki* extract to stand may be performed at a temperature between 0 and 20° C. for 5-30 hours. In still another embodiment of the present invention, allowing the *Broussonetia kazinoki* extract to stand may be performed at a temperature between 0 to 15° C. for 10-25 hours. By allowing the *Broussonetia kazinoki* extract to stand at low temperature, impurities can be precipitated, and the precipitated components are materials having low solubility in the solvent and do not influence the effect of the *Broussonetia kazinoki* extract, for example, the melanin production inhibitory or tyrosinase inhibitory effect. Thus, the effect of the *Broussonetia kazinoki* extract, for example, the melanin production inhibitory or tyrosinase inhibitory effect, can be further improved.

The method for preparing the *Broussonetia kazinoki* extract according to one embodiment of the present invention may further comprise, after the step of allowing the *Broussonetia kazinoki* extract at stand, a step of filtering the *Broussonetia kazinoki* extract to remove the precipitated insoluble components. In one embodiment of the present invention, the filtration may be performed using filter paper.

The method for preparing the *Broussonetia kazinoki* extract according to one embodiment of the present invention may further comprise a step of re-concentrating the filtered *Broussonetia kazinoki* extract. In one embodiment of the present invention, the re-concentration may be performed at a temperature of 80° C. or lower, particularly 60° C. or lower, until the volume of the extract reaches ½ to ⅓ of the volume before the re-concentration.

The method for preparing the *Broussonetia kazinoki* extract according to one aspect of the present invention comprises a step of crystallizing the *Broussonetia kazinoki* extract. In one embodiment of the present invention, the crystallization may be performed while the *Broussonetia kazinoki* extract is stirred in water at a temperature between −5 and 15° C. for 1-20 hours. In another embodiment of the present invention, the crystallization may be performed while the *Broussonetia kazinoki* extract is stirred in water at a temperature between 0 and 10° C. for 1-15 hours. In still another embodiment of the present invention, the crystallization may be performed while the *Broussonetia kazinoki* extract is stirred in water at a temperature between 0 and 7° C. for 1-10 hours. In still another embodiment of the present invention, water may be purified water that is used in an amount corresponding to 5-30 times, particularly 10-20 times, the volume of the *Broussonetia kazinoki* extract. As the amount of water added increases and the temperature of water decreases, the crystallization of the *Broussonetia kazinoki* extract easily occurs. When this crystallization process is performed, the effects of the *Broussonetia kazinoki* extract, for example, the tyrosinase inhibitory effect, can be further improved.

The method for preparing the *Broussonetia kazinoki* extract according to one embodiment of the present invention may further comprise, after a step of crystallizing the *Broussonetia kazinoki* extract, a step of allowing *Broussonetia kazinoki* extract to stand. In one embodiment of the present invention may be performed at a temperature between 0 and 10° C. for 10-30 hours. This process can facilitate the production of a precipitate in the extract. In another embodiment of the present invention, the method for preparing the *Broussonetia kazinoki* extract may comprise a step of removing the upper layer solution and collecting the crystallized *Broussonetia kazinoki* extract, when a precipitate is formed after allowing the *Broussonetia kazinoki* extract to stand.

The method for preparing the *Broussonetia kazinoki* extract according to one embodiment of the present invention may further comprise, after the step of collecting the crystallized *Broussonetia kazinoki* extract, a step of drying the *Broussonetia kazinoki* extract to obtain powder. The drying may be performed using any conventional drying method, particularly, a freeze-drying method.

The method for preparing the *Broussonetia kazinoki* extract according to one embodiment of the present invention may further comprise, after the step of crystallizing the *Broussonetia kazinoki* extract, a step of loading the *Broussonetia kazinoki* extract onto a carrier. When this loading step is performed, the stability of activity of an active ingredient in the *Broussonetia kazinoki* extract can be increased. The active ingredient includes an ingredient showing a skin whitening effect. Specifically, the active ingredient may be kazinol C.

In one embodiment of the present invention, the carrier comprises one or a mixture of two or more selected from the group consisting of polylactic acid (PLA), polyethyleneadipate (PEA), polymethylmethacrylate (PMMA), polybutylmethacrylate (PBMA), trimethylammoniumethylmethacrylate (TMAEMA), solid lipid nanoparticles (SLN)

and silica. In another embodiment of the present invention, the carrier comprises polylactic acid (PLA), a polybutylmethacrylate/trimethylammoniumethylmethacrylate (PBMA/TMAEMA) copolymer, polyethyleneadipate (PEA), polymethylmethacrylate (PMMA), solid lipid nanoparticles (SLN) or silica. When the *Broussonetia kazinoki* extract is loaded onto the above-described carrier, the stability thereof can be increased in an efficient and easy manner.

In one embodiment of the present invention, the *Broussonetia kazinoki* extract may be loaded in an amount of 0.01-30 wt % based on the weight of the carrier. In another embodiment of the present invention, the *Broussonetia kazinoki* extract may be loaded in an amount of 0.1-20 wt % based on the weight of the carrier. In still another embodiment of the present invention, the *Broussonetia kazinoki* extract may be loaded in an amount of 1.0-10 wt % based on the weight of the carrier. When the *Broussonetia kazinoki* extract is used in an amount within the above-specified range, the effects intended by the present invention can be sufficiently exhibited, and both the stability and safety of the extract can be satisfied, and also the use of the *Broussonetia kazinoki* extract within the above-specified range is preferable in terms of cost versus effect.

In one embodiment of the present invention, loading the *Broussonetia kazinoki* extract onto the carrier can be performed by any conventional method known in the art.

The method for preparing the *Broussonetia kazinoki* extract according to one embodiment of the present invention may further comprise, after the step of crystallizing the *Broussonetia kazinoki* extract, a step of collecting a skin whitening active ingredient from the *Broussonetia kazinoki* extract by high-speed counter current chromatography (HSCCC) using a two-phase solvent system. In another embodiment of the present invention, the skin whitening active ingredient includes kazinol C. In the method, the skin whitening active ingredient can be separated and collected using the difference in partition coefficient between components.

For more accurate separation, a two-phase solvent system, which is separated into 2 phases upon mixing and in which the partition coefficient of the skin whitening active ingredient is close to 1, can be selected from among solvents in which the skin whitening active ingredient can be easily dissolved. Herein, it is required that the partition coefficients of other components do not overlap with the partition coefficient of the skin whitening active ingredient.

In one embodiment of the present invention, the partition coefficient of the skin whitening active ingredient in the two-phase solvent system may be 0.90-1.10. In another embodiment of the present invention, the partition coefficient of the skin whitening active ingredient in the two-phase solvent system may be 0.95-1.05. In still another embodiment of the present invention, the partition coefficient of the skin whitening active ingredient in the two-phase solvent system may be 0.97-1.03.

In one embodiment of the present invention, the two-phase solvent system may comprise hexane, ethyl acetate, methanol and water. In another embodiment of the present invention, the two-phase solvent system may comprise hexane, ethyl acetate, methanol and water at a ratio of 1-10:1-10:1-10:1-10, particularly 1-5:1-5:1-5:1-5, more particularly 1-3:1-3:1-3:1-3. Herein, the ratio between the solvents may be weight or volume ratio.

In another aspect, the present invention provides a *Broussonetia kazinoki* extract for skin whitening prepared by the above-described method. The *Broussonetia kazinoki* extract is prepared by the method of the present invention, which comprises the steps of allowing the extract to stand at low temperature and inducing crystallization with stirring at low temperature, unlike conventional extraction methods. Thus, the *Broussonetia kazinoki* extract can include a skin whitening active ingredient at higher purity. The skin whitening active ingredient includes kazinol C. The *Broussonetia kazinoki* extract can have improved inhibitory effects on melanin production and tyrosinase activity compared to existing stances known to show skin whitening effects and can show a very excellent skin whitening effect.

Furthermore, the stability of activity of skin whitening active ingredients having unstable activity, for example, kazinol C, can be increased by the stabilization process of loading the *Broussonetia kazinoki* extract onto the carrier, and thus the *Broussonetia kazinoki* extract can have improved inhibitory effects on melanin production and tyrosinase activity, and improved skin whitening effects. In addition, the *Broussonetia kazinoki* extract loaded onto the carrier shows excellent skin safety, and thus can be used in a skin external composition.

In still another aspect, the present invention provides a skin external composition containing the *Broussonetia kazinoki* extract. The skin external composition contains the *Broussonetia kazinoki* extract containing skin whitening active ingredients having high purity and high stability of activity, and thus shows excellent inhibitory effects on melanin production and tyrosinase activity, and excellent skin whitening effects. In addition, the skin external composition does not cause skin abnormalities, and thus is used with safety.

In one embodiment of the present invention, the skin external composition containing the *Broussonetia kazinoki* extract includes a cosmetic composition.

The cosmetic composition may be provided as any formulation suitable for topical application. For example, the cosmetic composition can be provided in the form of a solution, oil-in-water emulsion, water-in-oil emulsion, suspension, solid, gel, paste, foam or aerosol composition. Such formulations can be prepared according to any conventional method known in the art.

The cosmetic composition may contain, in addition to the above component, other components capable of increasing the main effect of the composition, in the range that does not impair the main effect. The cosmetic composition according to the present invention may comprise a substance selected from the group consisting of vitamins, polypeptides, polysaccharides and sphingolipids. In addition, the cosmetic composition according to the present invention may comprise a moisturizer, an emollient, a surfactant, a UV absorber, a preservative, a disinfectant, an antioxidant, a pH adjuster, organic and inorganic pigments, a fragrance, a cooling agent or an anhidrotic agent. The contents of the above components in the cosmetic composition can be easily selected by a person skilled in the art in the range that does not impair the objects and effects of the present invention.

In one embodiment of the present invention, the skin external composition containing the *Broussonetia kazinoki* extract includes a pharmaceutical composition.

In one embodiment of the present invention, the formulation of the pharmaceutical composition may be a solid, a solution, a suspension, an emulsion, a gel, a patch or a spray, but is not limited thereto. The formulation of the pharmaceutical composition can be easily prepared using a surfactant, an excipient, a hydrating agent, an emulsifying agent, a suspending agent, a salt or buffer for osmotic pressure, a coloring agent, a flavoring agent, a stabilizer, a preservative or other conventional additives according to any conventional method known in the art.

The dose of the active ingredient of the pharmaceutical composition according to the present invention will vary depending on the age, sex and weight of the subjected to be administered, the condition or severity of the disease, the route of administration or the physician's judgment. Determination of the dose of the active ingredient based on such factors is within the level of those skilled in the art, and the daily dose of the active ingredient may be, for example, 0.001 mg/kg/day to 50 mg/kg/day, more specifically 0.1 mg/kg/day to 5 mg/kg/day, but is not limited thereto.

Hereinafter, the present invention will be described in further detail with reference to examples, comparative examples, preparation examples and test examples. However, these examples, comparative examples, preparation examples and test examples are for illustrative purposes only and are not intended to limit the scope of the present invention.

Test Example 1

Identification of Active Ingredient of *Broussonetia kazinoki* Extract

1. Identification of Kazinol C

In an ethanol extract of *Broussonetia kazinoki*, kazinol C (molecular weight: 464) was identified by mass spectroscopy and NMR analysis, and the content of kazinol C in the *Broussonetia kazinoki* extract was found to be 8-15%.

2. Method for Evaluation of Tyrosinase Inhibitory Effect 50 mg of a sample to be evaluated for tyrosinase inhibitory activity was dissolved in ethanol to make 100 ml of a solution. 10 ml of the solution was taken, and ethanol was added thereto to make 100 ml of a sample solution. 500 µl of a substrate solution, 450 µl of purified water and 50 µl of the sample solution are added to and mixed with 500 µl of buffer, and 50 µl of an enzyme (tyrosinase) solution is added to the mixture. The resulting mixture is allowed to react at 37° C. for 10 minutes, and then immediately allowed to stand on ice for 5 minutes, and the absorbance at 490 nm is measured. The tyrosinase inhibitory effect of the sample is evaluated based on the absorbance of the sample compared to the absorbance of a blank sample.

3. Relationship Between Kazinol C and Tyrosinase Inhibitory Effect

The content of kazinol C in the *Broussonetia kazinoki* extract was analyzed by HPLC, and the tyrosinase inhibitory effect was evaluated as a function of the content of kazinol C.

The results of the evaluation are shown in FIG. 1. As can be seen in FIG. 1, as the content of kazinol C in the *Broussonetia kazinoki* extract increased, the tyrosinase inhibitory effect also increased.

Test Example 2

Evaluation of Tyrosinase Inhibitory Effect

1. Evaluation of Tyrosinase Inhibitory Effect as a Function of Extraction Solvent 3 samples prepared by washing, drying and cutting the root bark of *Broussonetia kazinoki* were added to ethanol (Example 1), ethyl acetate (Comparative Example 1) and acetone (Comparative Example 2), respectively, and extracted at 60-80° C. for 4-6 hours, and then the yield of the extraction was evaluated. Next, the tyrosinase inhibitory effects of the three extracts were evaluated according to the method of Test Example 1-2. The results of the evaluation are shown in Table 1 below.

TABLE 1

| Solvent | Ethanol (Example 1) | Ethyl acetate (Comparative Example 1) | Acetone (Comparative Example 2) |
|---|---|---|---|
| Extraction yield (%) | 6.7 | 5.5 | 5.6 |
| Tyrosinase inhibitory effect (%) | 25.1 | 22.8 | 26.8 |

As can be seen from the results in Table 1 above, the use of ethanol as the solvent shows the highest extraction yield and an excellent tyrosinase inhibitory effect. Also, it is concluded that the use of ethanol as the solvent is preferable in that it can facilitate the production process. This suggests that, when alcohol is used as the extraction solvent, a *Broussonetia kazinoki* extract having an excellent tyrosinase inhibitory effect can be easily obtained in high yield.

2. Evaluation of Tyrosinase Inhibitory Effect as a Function of Extraction Method Four samples prepared by washing, drying and cutting the root bark of *Broussonetia kazinoki* and adding the cut root bark to ethanol were extracted at 80° C. for 4 hours (Example 2), at room temperature for 1 day (Comparative Example 3), at room temperature for 7 days (Comparative Example 4) and at room temperature for 3 weeks (Comparative Example 5), respectively, and the yield of the extraction was evaluated. The tyrosinase inhibitory effects of the four extracts were evaluated according to the method of Test Example 1-2. The results of the evaluation are shown in Table 2 below.

TABLE 2

| | Extraction method | | | |
|---|---|---|---|---|
| | Extraction at 80° C. for 4 hours (Example 2) | Extraction at room temperature for 1 day (Comparative Example 3) | Extraction at room temperature for 7 days (Comparative Example 4) | Extraction at room temperature for 3 weeks (Comparative Example 5) |
| Extraction yield (%) | 6.7 | 2.9 | 4.5 | 5.2 |
| Tyrosinase inhibitory effect (%) | 25.1 | 19.2 | 25.4 | 18.2 |

As can be seen from the results in Table 2 above, extraction at high temperature (80° C.) showed a high extraction yield and an excellent tyrosinase inhibitory effect compared to extraction at room temperature. In addition, extraction at high temperature is preferable in that a *Broussonetia kazinoki* extract having an excellent tyrosinase inhibitory effect can be prepared within a short time.

3. Evaluation of Tyrosinase Inhibitory Effect Resulting from Allowing Extract to Stand at Low-Temperature The ethanol extract of Example 1, obtained in Test Example 2-1, was allowed to stand at 4° C. for 12-24 hours. After impurities have been precipitated, they were removed, thereby obtaining an extract of Example 3. The tyrosinase inhibitory effect of the extract of Example 3 was evaluated according to the method of Test Example 1-2. The results of the evaluation are shown in Table 3 below.

TABLE 3

|  | Example 1 | Example 3 |
| --- | --- | --- |
| Tyrosinase inhibitory effect (%) | 25.1% | 31.6% |

As can be seen from the results in Table 3 above, when the extract was allowed to stand at low temperature (4° C.) after extraction, the tyrosinase inhibitory effect of the extract increased. In other words, the tyrosinase inhibitory effect of the *Broussonetia kazinoki* extract can be increased by allowing the extract to stand at low temperature after extraction. Meanwhile, the yield decreased from 6.7% to 5%, suggesting that impurities were effectively removed from the extract. This shows that materials having low solubility in ethanol were also extracted due to high temperature in the extraction process, and these impurities were effectively removed during the process of allowing the extract to stand at low temperature. The impurities that are precipitated during the process of allowing the extract to stand at low temperature showed little or no tyrosinase inhibitory effect. This indicates that a material having a tyrosinase inhibitory effect is not substantially lost during the process of allowing the extract to stand at low temperature.

4. Evaluation of Tyrosinase Inhibitory Effect Resulting from Crystallization A sample prepared by washing, drying and cutting the root bark of *Broussonetia kazinoki* was added to ethanol and extracted at 60-80° C. for 4-6 hours. Following this, the extract was allowed to stand at 4° C. for 12-24 hours to precipitate impurities which were then removed. Then, the extract was crystallized while it was stirred slowly at a temperature between 0 to 4° C. for 2-6 hours in purified water corresponding to 20 times the volume of the extract. The crystallized extract was collected, thereby obtaining an extract of Example 4. The tyrosinase inhibitory effect of the extract of Example 4 was evaluated according to the method of Test Example 1-2. In addition, the tyrosinase inhibitory effect of kojic acid as a control was evaluated. The results of the evaluation are shown in Table 4 below.

TABLE 4

|  | Example 4 | Control |
| --- | --- | --- |
| Tyrosinase inhibitory effect (%) | 95% | 80% |

As can be seen from the results in Table 4 above, when the *Broussonetia kazinoki* extract was crystallized by stirring in cold purified water, it had a very excellent tyrosinase inhibitory effect. In other words, when the *Broussonetia kazinoki* extract was dipped at low temperature, the tyrosinase inhibitory effect is significantly increased by crystallization. Meanwhile, the yield of the extract after the crystallization process was 3%, suggesting that impurities can be effectively removed by the crystallization process. The supernatant which was not crystallized in this process showed little or no tyrosinase inhibitory effect. This indicates that a material having a tyrosinase inhibitory effect is not substantially lost in the crystallization process.

Preparation Examples 1 to 7

Preparation of Carrier Compositions

1. Preparation of Polylactic Acid (PLA) Capsule Comprising 5 wt % of *Broussonetia Kazinoki* Extract 10 g of PLA and 0.2-0.3 g of stearyl alcohol were dissolved in 40 ml of methylene chloride, and 0.5 g of the *Broussonetia kazinoki* extract powder of Example 4 was added and dissolved therein. The solution was stirred in 400 ml of water containing 1 wt % of polyvinyl alcohol (PVA) dissolved therein. Methylene chloride was removed at room temperature under reduced pressure, and the residue was filtered and dried, thereby preparing a PLA capsule (Preparation Example 1) comprising the *Broussonetia kazinoki* extract.

2. Preparation of a Capsule Composed of a PLA Comprising 4 wt % of a *Broussonetia Kazinoki* Extract and a Polybutylmethacrylate/Trimethyl Ammonium Ethyl Methacrylate (PBMA/TMAEMA) Copolymer The method in this Preparation Example is a method in which the outermost layer of the PLA capsule comprising 5 wt % of the *Broussonetia kazinoki* extract, prepared in Preparation Example 1, is coated with a PBMA/TMAEMA copolymer. First, 10 g of a PBMA/TMAEMA copolymer was dissolved in 250 ml of ethanol, and 55 g of the PLA capsules were uniformly dispersed in 500 ml of water containing 1 wt % of PVA dispersed therein. The ethanol phase was added slowly to the water phase while the solution was stirred with a homogenizer at 5000 rpm. Ethanol was removed at 40° C. under reduced pressure, and the residue was filtered and dried, thereby preparing a capsule (Preparation Example 2) comprising the *Broussonetia kazinoki* extract.

3. Preparation of Polyethyleneadipate (PEA) Capsule Comprising 5 wt % of *Broussonetia Kazinoki* Extract 47.5 g of PEA was dissolved in 200 ml of methylene chloride, and 2.5 g of the *Broussonetia kazinoki* extract powder of Example 4 was added and dissolved therein. Then, the solution was added to 450 ml of water containing 1 wt % of PVA dissolved therein and was stirred with a homogenizer at 5000 rpm. Methylene chloride was removed at room temperature under reduced pressure, and the residue was filtered and dried, thereby preparing a PEA capsule (Preparation Example 3).

4. Preparation of Solid Lipid Nanoparticles (SLN) Comprising 2.5 wt % of *Broussonetia Kazinoki* Extract 15 g of beeswax and 2 g of hydrogenated lecithin were dissolved by heating to 70° C., and 2 g of the *Broussonetia kazinoki* extract powder of Example 4 was added and dissolved therein. The wax phase was added slowly to 60 g of water at 60° C. while the solution was stirred with a homogenizer, thereby preparing SLN (Preparation Example 4).

5. Preparation of Polymethylmethacrylate (PMMA) Capsule Comprising 5 wt % of *Broussonetia Kazinoki* Extract 10 g of PMMA was dissolved in 40 ml of methylene chloride, and 0.5 g of the *Broussonetia kazinoki* extract powder of Example 4 was added and dissolved therein. The solution was stirred in 400 ml of water containing 0.5 wt % of poloxamer 407 dissolved therein. Methylene chloride was removed at room temperature under reduced pressure, and the residue was filtered and dried, thereby preparing a PMMA capsule (Preparation Example 5).

6. Preparation of Polyethyleneadipate-Polymethylmethacrylate (PEA/PMMA) Capsule Comprising 5 wt % of *Broussonetia Kazinoki* Extract 23.75 g of PEA and 23.75 g of PMMA were dissolved in 200 ml of methylene chloride, and 2.5 g of the *Broussonetia kazinoki* extract powder of Example 4 was added and dissolved therein. The solution was added to 450 ml of water containing 1 wt % of PVA and was stirred with a homogenizer at 5000 rpm. Methylene chloride was removed at room temperature under reduced pressure, and the residue was filtered and dried, thereby preparing a PEA/PMMA capsule (Preparation Example 6).

7. Preparation of Silica Powder Comprising 5 Wt % of *Broussonetia Kazinoki* Extract The *Broussonetia kazinoki* extract was completely dissolved in ethanol, and mesoporous silica was added thereto and sufficiently stirred for 1-3 hours. The stirred solution was filtered and vacuum-dried at room temperature, thereby preparing mesoporous silica powder (Preparation Example 7) comprising the *Broussonetia kazinoki* extract Examples 5 to 11 and Comparative Example 6

In order to evaluate the stability of the active ingredient of the *Broussonetia kazinoki* extract loaded into the carrier, o/w-type emulsion formulations of Examples 5 to 11 and Comparative Example 6 having the compositions shown in Table 5 below were prepared using the capsules of Preparation Examples 1 to 7 according to a conventional method.

TABLE 5

| Components | Unit (wt %) | | | | | | | Comp. |
| --- | --- | --- | --- | --- | --- | --- | --- | --- |
| | Ex. 5 | Ex. 6 | Ex. 7 | Ex. 8 | Ex. 9 | Ex. 10 | Ex. 11 | Ex. 6 |
| *Broussonetia kasinoki* extract 5%/PLA | 0.8 | — | — | — | — | — | — | — |
| *Broussonetia kasinoki* extract 4%/PLA + (PBMA/TMAEMA) | — | 1 | — | — | — | — | — | — |
| *Broussonetia kasinoki* extract 5%/PEA | — | — | 0.8 | — | — | — | — | — |
| *Broussonetia kasinoki* extract 2.5%/SLN | — | — | — | 1.6 | — | — | — | — |
| *Broussonetia kasinoki* extract 5%/PMMA | — | — | — | — | 0.8 | — | — | — |
| *Broussonetia kasinoki* extract 5%/PEA + PMMA | — | — | — | — | — | 0.8 | — | — |
| *Broussonetia kasinoki* extract 5%/Silica | — | — | — | — | — | — | 0.8 | — |
| *Broussonetia kasinoki* extract | — | — | — | — | — | — | — | 0.04 |
| EDTA-2Na | 0.02 | 0.02 | 0.02 | 0.02 | 0.02 | 0.02 | 0.02 | 0.02 |
| Glycerin | 5 | 5 | 5 | 5 | 5 | 5 | 5 | 5 |
| Butylene glycol | 5 | 5 | 5 | 5 | 5 | 5 | 5 | 5 |
| Vegetable hydrogenated oil | 1.5 | 1.5 | 1.5 | 1.5 | 1.5 | 1.5 | 1.5 | 1.5 |
| Stearic acid | 0.6 | 0.6 | 0.6 | 0.6 | 0.6 | 0.6 | 0.6 | 0.6 |
| Glycerol stearate | 1 | 1 | 1 | 1 | 1 | 1 | 1 | 1 |
| Cetearyl alcohol | 2 | 2 | 2 | 2 | 2 | 2 | 2 | 2 |

TABLE 5-continued

| Components | Unit (wt %) | | | | | | | Comp. |
| --- | --- | --- | --- | --- | --- | --- | --- | --- |
| | Ex. 5 | Ex. 6 | Ex. 7 | Ex. 8 | Ex. 9 | Ex. 10 | Ex. 11 | Ex. 6 |
| arachidyl/behenyl alcohol & arachidyl glucoside | 1 | 1 | 1 | 1 | 1 | 1 | 1 | 1 |
| Cetylalcohol & cetearyl glucoside | 2 | 2 | 2 | 2 | 2 | 2 | 2 | 2 |
| Liquid paraffin | 6 | 6 | 6 | 6 | 6 | 6 | 6 | 6 |
| caprylic/capric triglyceride | 6 | 6 | 6 | 6 | 6 | 6 | 6 | 6 |
| Carbomer | 0.05 | 0.05 | 0.05 | 0.05 | 0.05 | 0.05 | 0.05 | 0.05 |
| Triethanolamine | 0.05 | 0.05 | 0.05 | 0.05 | 0.05 | 0.05 | 0.05 | 0.05 |
| Preservative, fragrance, pigment | q.s. | q.s. | q.s. | q.s. | q.s. | q.s. | q.s. | q.s. |
| Purified water | Balance | Balance | Balance | Balance | Balance | Balance | Balance | Balance |

The formulations of Examples 5 to 11 and Comparative Example 6 all contained the *Broussonetia kazinoki* extract in an amount of 0.04 wt % based on the total weight of the emulsion composition.

Test Example 3

Evaluation of Stability of Active Ingredient of *Broussonetia kazinoki* Extract

In order to evaluate whether the typical active ingredient kazinol C of the *Broussonetia kazinoki* extract is stabilized when the extract is loaded into the carrier, the content of kazinol C in each of the carrier compositions of Preparation Examples 1 to 7 and the o/w-type emulsions of Examples 5 to 11 and Comparative Example 6 was analyzed by HPLC.

The content of kazinol C was measured at the time point of the start of analysis and at one-month intervals for 4 months. The content of kazinol C was calculated relative to 100% for the time point of the start of analysis, and the results of the calculation are shown in Table 6 below.

TABLE 6

| | Carrier | | | | | | | | | | | | | |
| --- | --- | --- | --- | --- | --- | --- | --- | --- | --- | --- | --- | --- | --- | --- |
| | PLA | | PLA + (PBMA/TMAEMA) | | PEA | | SLN | | PMMA | | PEA + PMMA | | Silica | | No carrier |
| | Prep. Ex. 1 | Ex. 5 | Prep. Ex. 2 | Ex. 6 | Prep. Ex. 3 | Ex. 7 | Prep. Ex. 4 | Ex. 8 | Prep. Ex. 5 | Ex. 9 | Prep. Ex. 6 | Ex. 10 | Prep. Ex. 7 | Ex. 11 | Comp. Ex. 6 |
| 0 | 100 | 100 | 100 | 100 | 100 | 100 | 100 | 100 | 100 | 100 | 100 | 100 | 100 | 100 | 100 |
| Month 1 | 94 | 93 | 99 | 99 | 96 | 95 | 93 | 93 | 97 | 90 | 100 | 99 | 78 | 86 | 78 |
| Month 2 | 93 | 89 | 97 | 96 | 94 | 93 | 85 | 78 | 89 | 78 | 98 | 98 | 64 | 68 | 59 |
| Month 3 | 91 | 85 | 96 | 94 | 93 | 90 | 73 | 59 | 94 | 63 | 96 | 96 | 53 | 47 | 42 |
| Month 4 | 88 | 80 | 93 | 90 | 89 | 84 | 71 | 46 | 87 | 46 | 95 | 95 | 44 | 25 | 23 |

As can be seen from the results in Table 6 above, the contents of kazinol in Preparation Examples 1 to 7 and Examples 5 to 11 were all maintained at high levels compared to that in Comparative Example 6 even after the time has elapsed. In other words, it can be seen that, when the *Broussonetia kazinoki* extract is loaded into the carrier, the active ingredient thereof has high stability, and this high stability is maintained even when the *Broussonetia kazinoki* extract is formulated in the form of a cosmetic composition.

Test Example 4

Evaluation of Skin Safety

In order to examine the skin safety of the compositions of the above Examples, a patch test was performed on 18 adult women and 12 adult men (average age: 32.5).

At 28 hours after the attachment of the patch, the patch was removed, and at 30 minutes after the removal of the patch, first judgment was performed. After 96 hours, second judgment was performed. In order to examine the intensities of skin irritation of the compositions of the Examples and the Comparative Examples, the degree of the average response of the skin was determined by imparting weight according to the degree of the positive response of the skin. Also, the skin irritations of the compositions of the Examples and the Comparative Examples were visually judged, and the grade thereof was determined. The results are shown in Table 7 below.

TABLE 7

| Test material | Average response degree | Grade |
| --- | --- | --- |
| Example 5 | 0 | No irritation |
| Example 6 | 0 | No irritation |
| Example 7 | 0 | No irritation |
| Example 8 | 0 | No irritation |

TABLE 7-continued

| Test material | Average response degree | Grade |
|---|---|---|
| Example 9 | 0 | No irritation |
| Example 10 | 0 | No irritation |
| Example 11 | 0 | No irritation |
| Comp. Example 6 | 0 | No irritation |

As can be seen from the results in Table 7 above, the compositions of Examples 5 to 11 did not irritate the skin. Thus, it can be concluded that the cosmetic composition according to the present invention is safe to the skin.

Test Example 5

Evaluation of Whitening Effect of *Broussonetia Kazinoki* Extract (Cell Level)

1. Measurement of Cytotoxicity (1) Cell Culture

B16 melanoma cells from C57BL/6J (black, a/a) mouse melanoma were purchased from the Cell Line Bank. The cells were cultured in DMEM medium containing 10% fetal bovine serum (LONZA), 50 U/ml of penicillin and 50 μg/ml of 200 nM streptomycin under the conditions of 37° C. and 10% $CO_2$.

(2) Cytotoxicity Measurement (MTT Assay)

B16 melanoma cells were seeded in a 96-well plate at a density of $1\times10^4$ cells/well and cultured for 1 day. The medium was replaced with fresh medium containing each of arbutin and various concentration of the composition of Preparation Example 6, and the cells were cultured again for 24 hours. 50 μl of an MIT solution obtained by dissolving MIT in cell culture medium at a concentration of 2 mg/ml was added to each well, and medium was added to each well to a final volume of 200 μl, after which the cells were incubated for 3-4 hours. The medium was removed, and the produced formazan crystals were dissolved in 150 μl of DMSO, after which the absorbance of the formazan solution was measured at 540 nm. The measured absorbance was expressed as a percentage relative to the control (not treated with the test material) to evaluate whether the test sample has cytotoxicity. The results of the evaluation are shown in Table 8 below.

TABLE 8

| | Concentration (μg/ml) | % relative to control | Toxicity (%) |
|---|---|---|---|
| Arbutin | Control | 100 ± 4.3 | 0.0 |
| | 100 | 95.1 ± 4.8 | 4.9 |
| Preparation Example 6 | Control | 100 ± 4.5 | 0.0 |
| | 200 | 95.3 ± 2.6 | 4.7 |
| | 150 | 95.5 ± 2.3 | 4.5 |
| | 100 | 97.1 ± 2.3 | 2.9 |
| | 50 | 98.6 ± 3.7 | 1.4 |

As can be seen from the results in Table 8 above, the composition of Preparation Example 6 had no cytotoxicity at a concentration of 200 μg/ml or less, and arbutin had no cytotoxicity at a concentration of 100 μg/ml. Based on these results, the composition of Preparation Example 6 was tested at a concentration of 150 μg/ml or less, and arbutin was tested at a concentration of 100 μg/ml.

2. Evaluation of Inhibition of Melanin Production

B16 melanoma cells were seeded in a 24-well plate at a density of $4\times10^4$ cells/well and cultured overnight so as to adhere well to the plate. Then, medium containing 1 μM α-MSH for promoting melanin production and each concentration of the test sample of Preparation Example 6 or arbutin was added to each well. The plate was incubated for 72 hours, and then 200 μl of the cell culture medium was taken and the absorbance at 405 nm was measured. Based on the measurement, the amount of melanin was calculated. The calculated amount of melanin was expressed as a percentage relative to the control (not treated with the test material), and the results are shown in Table 9 below.

TABLE 9

| | Test sample concentration (μg/ml) | Melanin % relative to control | Inhibition (%) of melanin production | P value (relative to control) |
|---|---|---|---|---|
| Control | | 100 ± 4.9 | 0.0 | 1.0000 |
| Arbutin | 100 | 66.3 ± 4.7 | 33.7 | 0.0001 |
| Preparation Example 6 | 150 | 59.6 ± 3.4 | 40.4 | 0.0000 |
| | 100 | 68.1 ± 5.8 | 31.9 | 0.0002 |
| | 50 | 79.7 ± 3.7 | 20.3 | 0.0006 |

As can be seen from the results in Table 9 above, treatment with 150 μg/ml of the test sample of Preparation sample 6 showed a melanin production inhibition of 40.4% relative to the control, and treatment with 100 μg/ml of the test sample of Preparation sample 6 showed a melanin production inhibition of 31.9% relative to the control. Treatment with 100 μg/ml of arbutin showed a melanin production inhibition of 21.2%. This suggests that the *Broussonetia kazinoki* extract prepared according to the present invention has an excellent inhibitory effect on melanin production.

3. Evaluation of Inhibition of Tyrosinase Activity

A reaction solution containing reaction buffer (0.1M potassium phosphate buffer, pH 6.8), 0.03% L-tyrosine substrate solution (0.3 mg/ml in reaction buffer) and mushroom tyrosinase solution (2 unit/μl in reaction buffer) was prepared. First, as test samples, arbutin and the composition of Preparation Example 6 were prepared at various concentrations, and an enzyme was added thereto in an amount corresponding to 10 units, after which 0.1M phosphate buffer was added thereto to a final volume of 100 μl. 100 μl of 0.03% L-tyrosine substrate solution was added thereto, and then immediately, the absorbance at 475 nm was measured. Then, the mixture was allowed to react at 37° C. for 10 minutes, after which it was placed on ice to stop the reaction, and the absorbance was measured again. The change in absorbance for 10 minutes was compared with the control. The results are shown in Table 10 below.

TABLE 10

| | Concentration (μg/ml) | Tyrosinase inhibitory activity (%) relative to control | Inhibition (%) of tyrosinase activity | $IC_{50}$ (μg/ml) | P value |
|---|---|---|---|---|---|
| Control | | 100 ± 2.6 | 0.0 | | 1.000 |
| Arbutin | 500 | 12.3 ± 0.6 | 87.7 | 209.6 | 0.000 |
| | 250 | 43.5 ± 1.6 | 56.5 | | 0.000 |
| | 125 | 61.9 ± 2.2 | 38.1 | | 0.000 |

TABLE 10-continued

|  | Concentration (μg/ml) | Tyrosinase inhibitory activity (%) relative to control | Inhibition (%) of tyrosinase activity | IC$_{50}$ (μg/ml) | P value |
|---|---|---|---|---|---|
| Preparation Example 6 | 50 | 4.6 ± 0.5 | 95.4 | 23.7 | 0.000 |
|  | 25 | 22.4 ± 3.9 | 77.6 |  | 0.000 |
|  | 12.5 | 89.3 ± 9.1 | 13.0 |  | 0.017 |

As can be seen from the results in Table 10, the composition of Preparation Example 6 showed a statistically significant effect on the inhibition of tyrosinase activity compared to the control (not treated with the test sample), and this effect was superior to that of arbutin known to have an excellent effect on the inhibition of tyrosinase activity. The concentration (IC$_{50}$) at which tyrosinase activity is inhibited by 50% was 23.7 μg/ml for the composition of Preparation Example 6 and 209.6 μg/ml for arbutin.

This suggests that the *Broussonetia kazinoki* extract prepared according to the present invention has a very excellent effect on the inhibition of tyrosinase activity.

As a result, it can be seen that the *Broussonetia kazinoki* extract prepared according to the present invention has excellent effects on the inhibition of melanin production and tyrosinase activity, and thus has excellent skin whitening effects.

Test Example 6

Evaluation of Skin Whitening Effect of *Broussonetia Kazinoki* Extract (Clinical Evaluation)

Twenty three 18-60-year-old adult women were selected (average age: 42.17). UV light corresponding to 2.5 MED was irradiated onto two portions of the arm of each subject using Multiport Solar Simulator 601-300 W (Solar Light, USA) equipped with a 300 W xenon arc lamp, thereby inducing skin pigmentation. After 10 days, the o/w-type emulsion of Example 10 and a control (containing no *Broussonetia kazinoki* extract) were applied to the two portions, respectively. After application, visual evaluation by dermatologists and instrumental evaluation were performed at a temperature of 22~24° C. and a humidity of 40-60%. After 4, 6 and 8 weeks, visual evaluation by dermatologists, instrumental evaluation and questionnaire were performed.

1. Visual Evaluation by Dermatologists

Visual evaluation by dermatologists was performed by evaluating the degree of skin pigmentation on an 8-point scale (0 to 7; 7=the highest degree of skin pigmentation). The results of the evaluation are shown in Table 11 below.

TABLE 11

|  | Example 10 | | | | Control | | | |
|---|---|---|---|---|---|---|---|---|
|  | 0 week | 4 weeks | 6 weeks | 8 weeks | 0 week | 4 weeks | 6 weeks | 8 weeks |
| Mean | 4.87 | 3.35 | 2.54 | 2.02 | 4.74 | 3.35 | 2.83 | 2.56 |
| S.D. | 1.06 | 0.65 | 0.62 | 0.85 | 0.92 | 0.57 | 0.65 | 0.86 |

As can be seen from the results in Table 11 above, the degree of skin pigmentation at 4 weeks, 6 weeks and 8 weeks after application was lower in the emulsion of Example 10 than in the control. Also, the emulsion of Example 10 showed a high degree of skin pigmentation compared to the control. Such results suggest that the emulsion of Example 10 has a very excellent effect on the inhibition of pigmentation.

Thus, it can be seen that the *Broussonetia kazinoki* extract prepared according to the present invention has an excellent skin whitening effect.

2. Instrumental Evaluation

Instrumental evaluation was performed by measuring the L* value of the UV-radiated portion with Chromameter CR-400 (Minolta, Japan), and the results of the evaluation are shown in Table 12 below. Three measurements excluding the highest and lowest values among five measurements were averaged.

TABLE 12

|  | Example 10 | | | | Control | | | |
|---|---|---|---|---|---|---|---|---|
|  | 0 week | 4 weeks | 6 weeks | 8 weeks | 0 week | 4 weeks | 6 weeks | 8 weeks |
| Mean | 57.69 | 61.76 | 63.22 | 64.30 | 57.66 | 61.61 | 62.49 | 63.26 |
| S.D. | 3.32 | 2.29 | 2.29 | 2.31 | 3.81 | 1.87 | 1.90 | 1.85 |

In addition, instrumental evaluation was performed by melanin index (M.I.) using Mexameter MX18 (Germany). The results of the evaluation are shown in Table 13 below. Three measurements excluding the highest and lowest values among five measurements were averaged.

TABLE 13

|  | Example 10 | | | | Control | | | |
| --- | --- | --- | --- | --- | --- | --- | --- | --- |
|  | 0 week | 4 weeks | 6 weeks | 8 weeks | 0 week | 4 weeks | 6 weeks | 8 weeks |
| Mean | 232.38 | 201.45 | 178.91 | 164.23 | 233.60 | 204.39 | 182.88 | 172.52 |
| S.D. | 56.82 | 39.22 | 38.74 | 39.65 | 44.58 | 30.34 | 30.50 | 30.60 |

As can be seen from the results in Tables 12 and 13 above, the lightness of the skin at 4, 6 and 8 weeks after application was higher in the emulsion of Example 10 than in the control. Thus, it can be seen that the *Broussonetia kazinoki* extract prepared according to the present invention has an excellent skin whitening effect.

3. Questionnaire

Throughout the test period, whether the skin color of the applied portion became lighter, whether the area of the pigmentation portion decreased and whether the skin texture became softer were evaluated by the subjects on a 5-point scale (0 to 4) where higher points indicate more favorable changes. The percentage of subjects corresponding to each point is shown in the following Tables.

TABLE 14

Whether skin color became lighter

|  | Point | Example 10 (%) | Control (%) |
| --- | --- | --- | --- |
| 4 weeks | 0 | 0.0 | 0.0 |
|  | 1 | 21.7 | 34.8 |
|  | 2 | 43.5 | 43.5 |
|  | 3 | 34.8 | 17.4 |
|  | 4 | 0.0 | 4.3 |
| 6 weeks | 0 | 0.0 | 0.0 |
|  | 1 | 17.4 | 13.0 |
|  | 2 | 30.4 | 39.1 |
|  | 3 | 43.5 | 39.1 |
|  | 4 | 8.7 | 8.7 |
| 8 weeks | 0 | 0.0 | 0.0 |
|  | 1 | 4.3 | 4.3 |
|  | 2 | 21.7 | 26.1 |
|  | 3 | 56.5 | 47.8 |
|  | 4 | 17.4 | 21.7 |

TABLE 15

Whether area of pigmentation portion decreased

|  | Point | Example 10 (%) | Control (%) |
| --- | --- | --- | --- |
| 4 weeks | 0 | 13.0 | 13.0 |
|  | 1 | 17.4 | 17.4 |
|  | 2 | 43.5 | 52.2 |
|  | 3 | 26.1 | 17.4 |
|  | 4 | 0.0 | 0.0 |
| 6 weeks | 0 | 4.3 | 4.3 |
|  | 1 | 21.7 | 17.4 |
|  | 2 | 30.4 | 34.8 |
|  | 3 | 43.5 | 39.1 |
|  | 4 | 0.0 | 4.3 |
| 8 weeks | 0 | 4.3 | 0.0 |
|  | 1 | 17.4 | 4.3 |
|  | 2 | 39.1 | 26.1 |
|  | 3 | 39.1 | 47.8 |
|  | 4 | 0.0 | 21.7 |

TABLE 16

Whether skin texture became softer

|  | Point | Example 10 (%) | Control (%) |
| --- | --- | --- | --- |
| 4 weeks | 0 | 8.7 | 8.7 |
|  | 1 | 21.7 | 26.1 |
|  | 2 | 60.9 | 56.5 |
|  | 3 | 8.7 | 8.7 |
|  | 4 | 0.0 | 0.0 |
| 6 weeks | 0 | 4.3 | 4.3 |
|  | 1 | 17.4 | 13.0 |
|  | 2 | 39.1 | 52.2 |
|  | 3 | 39.1 | 30.4 |
|  | 4 | 0.0 | 0.0 |
| 8 weeks | 0 | 0.0 | 0.0 |
|  | 1 | 4.3 | 8.7 |
|  | 2 | 30.4 | 30.4 |
|  | 3 | 60.9 | 52.2 |
|  | 4 | 4.3 | 8.7 |

As can be seen from the results in Tables 14 to 16 above, when the emulsion of Example 10 was applied, the skin color of the UV-radiated potion became lighter, the area of the pigmentation portion decreased and the skin texture became softer, compared to when the control was applied.

4. Abnormalities

Throughout the test period, the portion to which the emulsion of Example 10 did not show contact dermatitis symptoms or other abnormalities. This suggests that the composition of Example 10 is suitable for use on the skin.

In addition, it can be seen that, when a skin external composition comprising the *Broussonetia kazinoki* extract prepared according to the present invention is applied to the human body, it shows the effects of alleviating skin pigmentation and whitening the skin.

Test Example 7

Separation of Kazinol C

1: Selection of Two-Phase Solvent System

Hexane/ethyl acetate/methanol/water mixtures having various compositions were tested. As a result, it was found that, when hexane/ethyl acetate/methanol/water had a ratio of 5/5/5/2, the partition coefficient of kazinol C was shown to be 0.997 (very close to 1) and did not overlap with the partition coefficients of other components.

The partition coefficient of kazinol C was measured in the following manner First, 1 mg of the extract of Example 3 was placed in a 10-ml test tube, and 2 ml of each of the upper layer solution and lower layer solution of a two-phase solution system, which reached equilibrium, was added thereto, and the mixture was shaken intensively for 1 minute. After the two phases have reached equilibrium, 100 µl of each of the upper layer solution and the lower layer solution was taken, dried, dissolved in 1 ml of ethanol, and analyzed by HPLC. The value obtained by dividing the amount of kazinol C in the upper layer solution by the amount of kazinol C in the lower layer solution was determined as partition coefficient.

2. Separation by HSCCC

HSCCC (high-speed counter current chromatography) TBE-1000A was used. First, the upper layer solution as a stationary phase was filled in the coil column at a flow rate of 10 ml/min, and the lower layer solution as a mobile phase was pumped into the coil at a flow rate of 5 ml/min while the device was rotated at 400 rpm. When the mobile phase started to flow out, liquid-liquid equilibrium was determined to be reached. When equilibrium was reached, 50 ml of a solution containing 0.5 g of the extract of Example 3 was injected. Separation temperature was maintained at room temperature. The liquid flowing out from the coil column outlet was passed through a 280 nm UV detector to obtain a fraction.

3. HPLC Analysis

Figure 2:
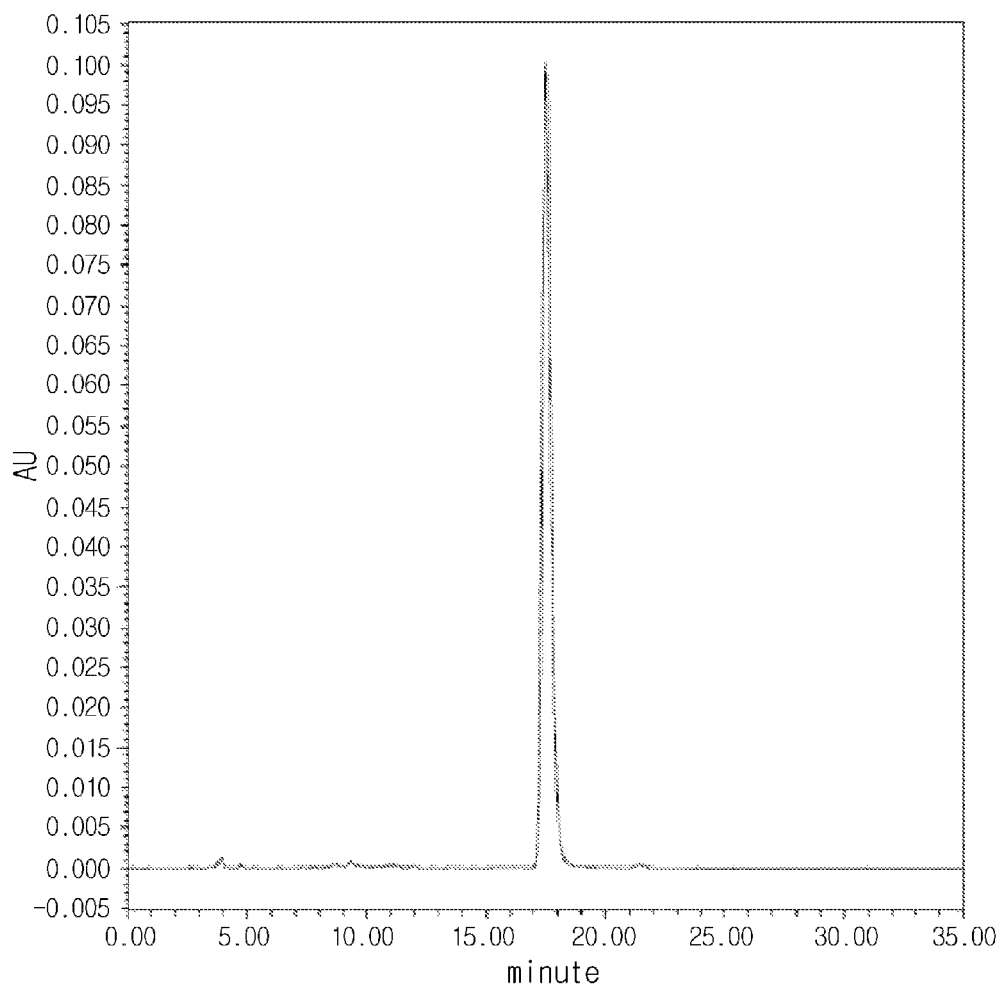
FIG. 2 is a graph showing the results of HPLC analysis that indicate that a HSCCC fraction contains kazinol C.

The HSCCC fraction was analyzed, and the results of the analysis are shown in FIG. 2. As can be seen in FIG. 2, the HSCCC fraction contained a very high purity of kazinol C, suggesting that kazinol C was separated from the extract.

The invention claimed is:

1. A method for preparing and processing a *Broussonetia kazinoki* extract, comprising the steps of:
   (1) extracting *Broussonetia kazinoki* with solvent;
   (2) allowing the *Broussonetia kazinoki* extract resulting from step (1) to stand;
   (3) crystallizing the *Broussonetia kazinoki* extract resulting from step (2);
   (4) obtaining a skin whitening active ingredient from the *Broussonetia kazinoki* extract resulting from step (3) by HSCCC (high-speed counter current chromatography) using a two-phase solvent system wherein the skin whitening active ingredient includes kazinol C; and
   (5) loading the skin whitening active ingredient resulting from step (4) into a carrier wherein the carrier is a mixture of polyethyleneadipate (PEA) and polymethylmethacrylate (PMMA), and wherein the carrier is in the form of a capsule such that the active ingredient is encapsulated by the carrier.

2. The method of claim 1, wherein the *Broussonetia kazinoki* includes the root bark of *Broussonetia kazinoki*.

3. The method of claim 1, wherein the solvent includes alcohol.

4. The method of claim 1, wherein the extraction is performed at a temperature between 50 to 100° C. for 1-10 hours.

5. The method of claim 1, wherein the step of allowing the *Broussonetia kazinoki* extract to stand is performed at a temperature between −5 and 25° C. for 1-40 hours.

6. The method of claim 1, wherein the step of crystallizing the *Broussonetia kazinoki* extract comprises stirring the *Broussonetia kazinoki* extract in water at a temperature between −5 and 15° C. for 1-20 hours.

7. The method of claim 1, wherein the *Broussonetia kazinoki* extract is used in an amount of 0.01-30 wt% based on the weight of the carrier.

8. The method of claim 1, wherein the two-phase solvent system includes hexane, ethyl acetate, methanol and water at a ratio of 1-10:1-10:1-10:1-10.

* * * * *